United States Patent [19]
Gramer

[11] Patent Number: 6,001,585
[45] Date of Patent: Dec. 14, 1999

[54] MICRO HOLLOW FIBER BIOREACTOR

[75] Inventor: Michael J. Gramer, Lino Lakes, Minn.

[73] Assignee: Cellex Biosciences, Inc., Coon Rapids, Minn.

[21] Appl. No.: 08/970,332

[22] Filed: Nov. 14, 1997

[51] Int. Cl.$^6$ .............................. C12Q 1/02; C12N 5/00; C12M 1/00; C12M 3/00

[52] U.S. Cl. .............................. 435/29; 435/41; 435/182; 435/243; 435/325; 435/382; 435/289.1; 435/297.1; 435/297.4; 435/400

[58] Field of Search .................................. 435/29, 34, 41, 435/174, 177, 182, 243, 395, 289.1, 325, 382, 297.1, 297.4, 400

[56] References Cited

U.S. PATENT DOCUMENTS

| | | | |
|---|---|---|---|
| 4,391,912 | 7/1983 | Yoshida et al. | 435/241 |
| 5,342,765 | 8/1994 | Irvine et al. | 435/71.1 |
| 5,622,857 | 4/1997 | Goffe | 435/378 |

OTHER PUBLICATIONS

Hirschel and Gruenberg, "An Automated Hollow Fiber System for the Large Scale Manufacture of Mammalian Cell Secreted Product". In *Large Scale Cell Culture Technology*; Lydersen, B., Ed.; 1988; pp. 113–144.

Jackson et al., "Evaluation of Hollow Fiber Bioreactors as an Alternative to Murine Ascites Production for Small Scale Monoclonal Antibody Production", *J. Immunol. Methods* 1996, 189, 217–231.

Lister et al., "Importance of β–lactamase Inhibitor Pharmacokinetics in the Pharmacodynamics of Inhibitor–Drug Combinations: Studies with Piperacillin–Tazobactum and Piperacillin–Sulbactam" in *Animicrob. Agents Chemother*, 1997, 41, 721–727.

Maki et al., "Treatment of Diabetes by Xenogenic Islets Without Immunosuppression: Use of a Vascularized Bioartificial Pancreas". *Diabetes* 1996, 45, 342–347.

Moore et al., "Activity of (s)–1–(3–Hydroxy–2–Phosphonylmethoxypropyl) Cytosine against Human Cytomegalovirus when Administered as a Single Bolus Dose and Continuous Infusion in In Vitro Cell Culture Perfusion System". *Antimicrob. Agents Chemother*.1994, 38, 2404–2408.

Piret and Cooney, "Model of Oxygen Transport Limitations in Hollow Fiber Bioreactors". *Biotech. Bioeng.* 1991, 37, 80–92.

Sardonini and Dibiasio, "Investigation of the Diffusion–Limited Growth of Animal Cells Around Single Fibers". *Biotech Bioeng.* 1992, 40, 1233–1242.

Schlapfer et al., "Development of Optimized Transfectoma Cell Lines for Production of Chimeric Antibodies in Hollow Fiber Cell Culture Systems", *Biotech. Bioeng.*, 1995, 45, 310–319.

Sielaff et al., "Gel–Entrapment Bioartifical Liver Therapy in Galactosamine Hepatitis". *J. Surg. Res.* 1995, 59, 179–184.

Stanness et al., "A Dynamic Model of the Blood–Brain Barrier In Vitro". *Neurotoxicology* 1996, 17, 481–496.

*Primary Examiner*—David M. Naff
*Attorney, Agent, or Firm*—Schwegman, Lundberg, Woessner & Kluth, P.A.

[57] ABSTRACT

A "micro" hollow fiber bioreactor and method of use are provided for use in screening different cell lines and process conditions. The bioreactor includes the use of an oxygen permeable (e.g., silicone rubber) tube sealably containing a hollow fiber bundle, in order to create an extracapillary space to provide a medium reservoir and an intracapillary space for the growth of cells. The bioreactor avoids the need for oxygen or medium pumps or supply systems, and permits multiple cell lines, and/or multiple conditions to be evaluated simultaneously. Preferably, the tube has an oxygen permeability of between about $100\times10^{-10}$ to about $10,000\times 10^{-10}$ (cc-mm/sec-cm$^2$-cm Hg), the extracapillary space provides a medium reservoir of about 1 ml to about 100 ml, the intracapillary space provides a cell culture volume of about 0.1 ml to about 1 ml, the hollow fibers have a molecular weight cut off from about 1 kD to about 1,000 kD and a pore size of from about 0.01 microns to about 5 microns, and the tube contains about 1 to about 1000 hollow fibers.

16 Claims, 12 Drawing Sheets

MICRO HOLLOW FIBER BIOREACTOR

TECHNICAL FIELD

The present invention relates to hollow fiber bioreactors. In another aspect, the invention relates to the use of bioreactors for producing and recovering biological compounds, expanding cell lines and/or for harvesting cells. In yet another aspect, the invention relates to materials and methods for screening cells lines to determine their adaptability to hollow fiber bioreactors.

BACKGROUND OF THE INVENTION

Hollow fiber bioreator technology is an economical alternative to traditional cell culture methods for the production of cells and cell-derived products (Hirschel and Gruenberg, "An Automated Hollow Fiber System for the Large Scale Manufacture of Mammalian Cell Secreted Product". *In Large Scale Cell Culture Technology*; Lydersen, B., Ed.; 1988; pp. 113–144), and is finding increased use for novel applications in the fields of tissue engineering (Maki et al., "Treatment of Diabetes by Xenogenic Islets Without Immunosuppression: Use of a Vascularized Bioartificial Pancreas". Diabetes 1996, 45, 342–347; Sielaff et al., "Gel-Entrapment Bioartificial Liver Therapy in Galactosamine Hepatitis". *J Surg. Res.* 1995, 59, 179–184), toxicology (Stanness et al., "A Dynamic Model of the Blood-Brain Barrier In Vitro". *Neurotoxicology* 1996, 17, 481–496), and pharmacology (Lister et al., "Importance of β-lactamase Inhibitor Pharmacokinetics in the Pharmacodynamics of Inhibitor-Drug Combinations: Studies with Piperacillin-Tazobactum and Piperacillin-Sulbactam" in *Animicrob. Agents Cheinother*, 1997, 41, 721–727; Moore et al., "Activity of (s)-1-(3-Hydroxy-2-Phosphonylmethoxypropyl) Cytosine against Human Cytomegalovirus when Administered as a Single Bolus Dose and Continuous Infusion in In Vitro Cell Culture Perfusion System". *Antimicrob. Agents Chemother*. 1994, 38, 2404–2408).

A diagram of a simple hollow fiber system is shown in FIG. 1. Cells are typically inoculated into the area outside of the hollow fibers, i.e., into the extracapillary (EC) space. Medium is circulated from a reservoir, through a pump, gas exchange cartridge, in order to pass through the fibers and within the intracapillary (IC) space, to be finally returned to the reservoir. For instance, Yoshida et al. (U.S. Pat. No. 4,391,912) describes a method of cultivating cells that involves the use of culture medium in a bioreactor having a shell and a plurality of hollow fibers, wherein the medium passes through the interior of the fibers and cells are cultivated in the space between the shell and the fibers.

Yet another approach is taken in the line of Tricentric™ bioreactors available from Setec, Livermore Calif. These bioreactors employ a concentric "fiber-within-fiber" geometry in which all cells are said to be grown within 100 microns of a nutrient source. More recent advances in this area are described, for instance, in U.S. Pat. No. 5622857, R. Goffe, which describes a high performance hollow fiber bioreactor having concentric hollow fiber bundles, a central hollow fiber bundle supplies media, and an outer array supplies oxygen needed for cell culture. The bioreactor is said to be useful for expanding therapeutic cells such as stem cells ex vivo, and as an extracorporeal device such as an artificial liver.

Typically, the hollow fiber membranes that serve to separate the cells and the circulating medium provide a predetermined molecular weight cutoff, e.g., allowing the passage of molecules having a molecular weight of under about 10 kD, while preventing the passage of larger molecules and cells themselves. Therefore, with cells being maintained in the EC space, nutrients such as glucose and oxygen are delivered in medium and passed through the fibers. The nutrients are able to pass through the fibers to be fed to the cells, while waste products such as lactate and carbon dioxide can pass through as well to be removed through the fibers and diluted in the medium reservoir. Large molecular weight growth factors in serum (or serum-free medium components such as transferring and albumin) can be supplied by the medium directly to the EC space containing the cells. The IC medium reservoir is changed every day or two to provide fresh basal nutrients. The EC medium is also changed every few days to replenish the high molecular weight growth factors and to harvest whatever product may be retained on the EC side along with the cells.

Occasionally, bioreactors have been described in which cells are grown in the IC, rather than EC, space. See, for instance, Sielaff et al. cited above. While these approaches generally provide improved flow distribution, they also suffer from several potential drawbacks as well, including poorer cell retention and reduced cell culture volume.

There are a number of advantages to using hollow fiber perfusion bioreactors for the production of proteins using mammalian cells. These advantages include the direct result of cell retention and the high density cell growth that hollow fiber systems provide. The use of a semi-permeable membrane to retain high molecular weight proteins on the cell side allows for more efficient use of expensive medium components while producing a highly concentrated product. As a result, cost reductions are obtained through continuous production, lower overhead, lower labor, reduced medium costs, and lower purification costs.

Since the presence of an ample supply of oxygen is generally considered the limiting factor in hollow fiber systems (see, e.g., Piret and Cooney, "Model of Oxygen Transport Limitations in Hollow Fiber LBioreactors". *Biotech. Bioeng*. 1991, 37, 80–92), it is common to provide the bioreactor with both continual IC medium (or EC medium, in the case of IC cell growth) recirculation as well as an in-line gas exchanger. The oxygen supply system is housed in a $CO_2$ incubator for pH buffering and temperature control. More sophisticated, dedicated systems include additional process controls such as automatic pH control, continuous medium replacement, and other strategies to optimize production (Hirschel and Gruenberg, cited above).

A continuing weakness of hollow fiber technology is an inherent lack of predictability, since there is no efficient screening method to determine how well a new cell line will perform in a hollow fiber system, or how well an established cell line will perform under new conditions. Instead, it is usually necessary to go through the costly and time consuming processing of complete scale up, on a cell line by cell line basis, in order to determine performance. Commercially available bioreactors are too large and expensive for simple screening protocols. Even small, inexpensive bioreactors are not well-suited for screening protocols since a pump is required to support the oxygen demand for each bioreactor.

Data from 96-well plates or T-flask cultures are useful for predicting cell line performance in stirred-tank reactors. Such data, however, does not correlate well with cell growth and productivity in high density hollow fiber cultures (Schlapfer et al., "Development of Optimized Transfectoma Cell Lines for Production of Chimeric Antibodies in Hollow Fiber Cell Culture Systems", *Biotech. Bioeng.*, 1995, 45, 310–319). Research to understand the fundamental mechanisms that affect cell productivity in hollow fiber culture is very complex, especially since several potentially critical factors are likely to be cell line dependent. How a particular cell line will react, for instance, to the partition of medium components across the membrane and to other stresses of high density culture is not well-understood.

This lack of understanding is due, in part, to the lack of a good model system for fundamental research and process development. One approach to hollow fiber research is to use a small system such as that shown in FIG. 1 (Jackson et al., "Evaluation of Hollow Fiber Bioreactors as an Alternative to Murine Ascites Production for Small Scale Monoclonal Antibody Production", *J. Immunol. Methods* 1996, 189, 217–231; Schlapfer et al., cited above). However, these systems are still too expensive for routine development, and cell growth takes several weeks to reach confluency. As a result, research proceeds very slowly, and replicates are often omitted so that the significance of the results is unknown. Very small hollow fiber bioreactors with only one or a few fibers have been used for fundamental research (Sardonini and Dibiasio, "Investigation of the Diffusion-Limited Growth of Animal Cells Around Single Fibers". *Biotech Bioeng.* 1992, 40, 1233–1242). However, each bioreactor still requires an independent flow circuit and medium recirculation pump to meet the cellular oxygen demand. As a result, this type of system is not well-suited for use as a screening tool.

What is clearly needed is a method and apparatus for screening cell lines in a manner that will inexpensively and quickly predict their use in a hollow fiber system.

SUMMARY OF THE INVENTION

The present invention provides a "micro" hollow fiber bioreactor that addresses and solves the need for efficient screening of different cell lines and process conditions. In a preferred embodiment, the bioreactor provides an optimal combination of cost and disposability, ease of use, and lack of pumps or other dedicated systems for the delivery of oxygen or medium. The use of two or more bioreactors of this invention permits a plurality of cell lines and/or culture conditions to be evaluated simultaneously. The micro bioreactor and related methods of preparing and using such a bioreactor can be used to screen and/or characterize the growth and metabolic activity of cell lines such as hybridoma cell lines. The bioreactor and related method can also be used to predict the effect of different media, or other conditions or parameters, for growth of a cell line in a production scale hollow fiber system.

In a preferred embodiment, the invention provides a hollow fiber bioreactor comprising:
  a) an oxygen permeable tube, preferably silicone rubber tubing, having first and second ends,
  b) a bundle of hollow fibers disposed within and traversing the length of the tube, substantially along the central axis thereof, thereby creating an IC space and an EC space, and
  c) first and second headers disposed at the first and second ends of the tube, respectively, for sealably securing the hollow fiber bundle and for perrnitting the passage of substances such as cells or nutrient media into the IC space and/or EC space.

In a particularly preferred embodiment, the bioreactor provides relative capacities (IC and EC) and overall dimensions (e.g., distance from the inner surface of the tubing to the outer surface of the bundle) that facilitate the transfer of oxygen through the tubing and to the hollow fiber bundle. The EC space, in turn, can provide a self-contained supply of medium that is suitable to maintain cell growth over the course of its intended use.

The present invention further provides a method of making a bioreactor, and a method of using a bioreactor. In another aspect, the invention provides a bioreactor as described herein having cells and medium within the IC space, and medium within the EC space.

The invention further provides a method for screening cells, the method comprising the steps of providing a bioreactor as described herein, filling the EC space with medium and inoculating the IC space with cells in medium, incubating the filled and inoculated bioreactor under conditions suitable to establish cell growth, and finally, assaying for cell growth. Finally, the invention provides a population of expanded cells and/or a biopharmaceutical produced by cells, wherein such cells were expanded or initially screened, respectively, using a bioreactor of this invention.

DETAILED DESCRIPTION

Figure 1:
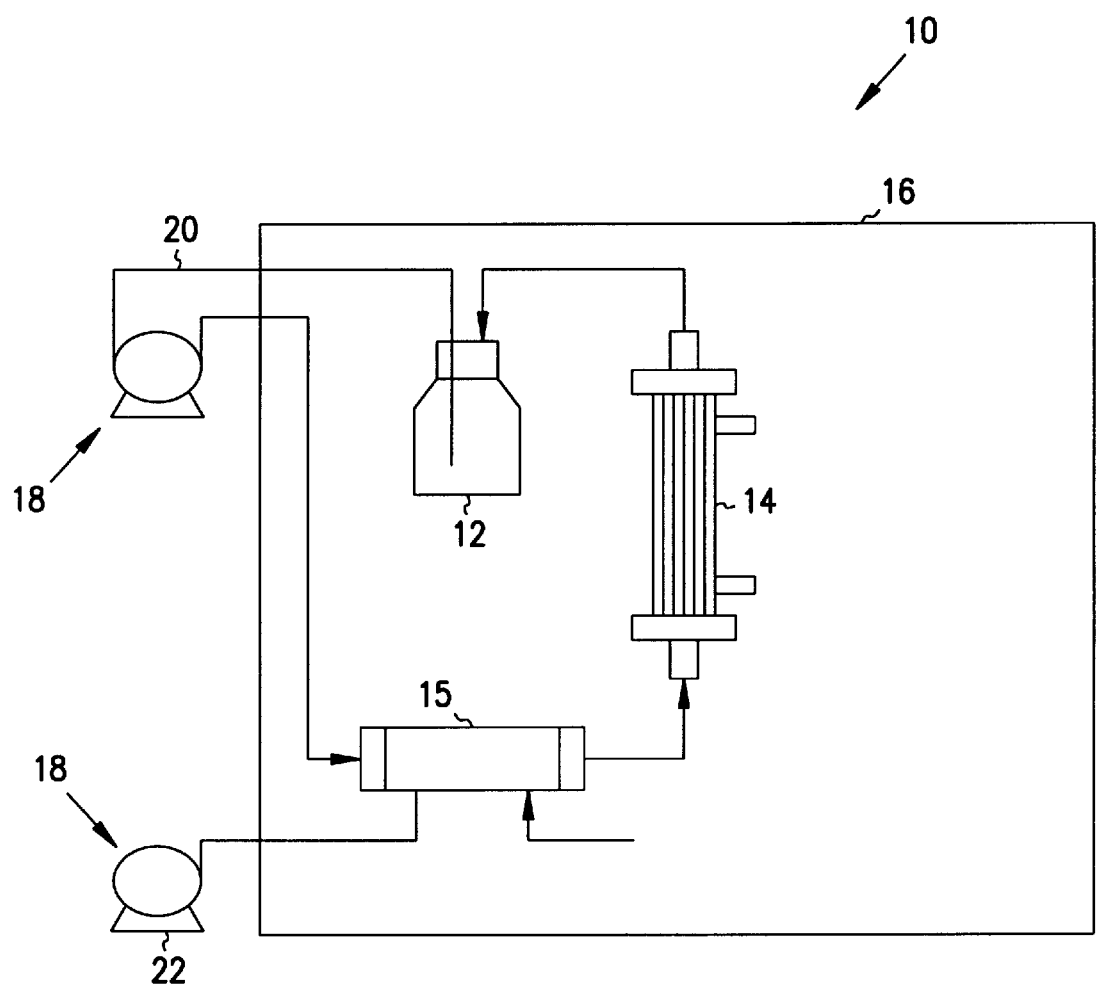
FIG. 1 depicts a schematic of a simple hollow fiber bioreactor of a type known in the prior art.

Applicant has discovered that a bioreactor of the type described herein is able to provide sufficient oxygenation directly through oxygen permeable tubing, thereby obviating the need for a separate or elaborate pump or system for medium recirculation. As a result, many cell lines and/or conditions can be tested simultaneously, easily, and inexpensively in a single incubator.

In a particularly preferred embodiment, the EC space provides a medium reservoir of sufficient capacity to feed the cells for at least 24 hours, while the walls of a silicone tube are sufficiently gas permeable to themselves serve as an oxygenation source. The hollow fiber bundle can be provided, for instance, by potting a plurality of fibers within luer T fittings, which in turn can be secured as headers within a piece of silicone tubing. The fibers are sufficient to provide an IC space having a volume of about 0.1 to about 1 ml. The actual volume will depend largely on the length of the fiber bundle, with the upper end of the range being limited (if at all) largely by the ability to fill the IC with medium and cells.

The EC space between the fibers and the silicone tubing, in turn, is large enough to serve as the medium reservoir (e.g., about 1 to about 100 ml), but still small enough to allow adequate diffusion of gasses between the silicone tubing and the fibers. Medium can be added to and removed from the bioreactor, through the headers, using syringes or other suitable delivery means. In use, a bioreactor can be flushed and filled with medium, inoculated with cells, and placed in an incubator for 1 to 3 days, or more, after which the bioreactor is harvested for analysis. Surprisingly, the permeability of the silicone tubing itself, given the respective capacities and other characteristics of the EC and IC spaces, is sufficient to provide the cells with a suitable level of oxygen.

For example, three days after inoculation at $5\times10^6$ cells/ml in a bioreactor of this invention, rho 1D4 murine hybridoma cells reached $2.8\times10^7$ cells/ml with an antibody concentration of 0.17 mg/ml. When inoculated at $5\times10^7$ cells/ml, the cell concentration reached $1.8\times10^8$/ml after three days with an antibody concentration of 1 mg/ml. Results from a series of experiments with the micro bioreactor suggested that the initial growth phase of this cell line in a hollow-fiber system is dependent on the serum concentration in the medium reservoir. This was confirmed by simultaneously inoculating two production-scale hollow fiber bioreator systems. The cell side of the membrane for each bioreactor contained 10% serum, but serum was added to the reservoir side of only one of the bioreactors. The cells with only basal medium in the reservoir died after a few days, while the cells with 10% serum in the medium reservoir grew rapidly. These results demonstrate that bioreactor of this invention can support good cell growth, and that it can be used as a research tool to predict the performance of large-scale hollow fiber systems.

A preferred bioreactor of this invention does not require the use of a separate oxygenation system, such as a pump, or a separate medium system or pump. The bioreactor instead involves the use of relatively small cell culture space together with low dead volume headers, in combination with a medium reservoir to feed the cells for at least 24 hours, and an oxygenation source. With the cells inoculated into the small IC space, the EC space between the fibers and the silicone tubing is large enough to serve as the medium reservoir, but still small enough to allow adequate diffusion of grasses between the silicone tubing and the fibers.

The bioreactor can support good cell growth, and can be used as a research tool to predict the performance of large-scale hollow fiber systems. For instance, the bioreactor can be used as an efficient screening tool to determine how well a new cell line will perform in a hollow fiber system, or how well an established cell line will perform under new conditions. Potential applications include: screening subclones for better producers in hollow fiber bioreactors; optimizing medium formulation, cell inoculation protocol, and culture temperature; determining the effect of hollow fiber type and porosity on cell growth and productivity; and determining if new cell types will grow well in hollow fiber bioreactors. The bioreactor can also be used for rapidly testing novel applications of hollow fiber technology in the fields of tissue engineering, vaccine production, gene therapy, toxicology, and pharmacology.

Although the present bioreactor is not able to reproduce or mimic all aspects of its larger, more elaborate brethren, it nevertheless provides an effective and inexpensive screening tool prior to the use of such elaborate systems, as well as a tool that can be used in the field or under other circumstances when such larger systems are not available. The present bioreactor, for instance, is not able to mimic the process control schemes of some of the more automated hollow fiber systems. These include control of pH, continuous addition and removal of both EC and IC media, and process control schemes to help mix the high molecular weight components on the cell side of the membrane. Moreover, the ratio of fiber surface area to cell culture volume will generally be fixed in the present bioreactor, for a given fiber diameter, since the cells are inoculated to the IC space, in contrast to larger scale bioreactors in which cells are typically inoculated into the EC space, and the fiber surface area to cell culture volume can be optimized by changing the fiber packing density.

On the other hand, the present bioreactor provides a rapid and inexpensive means to screen many different cell lines and conditions for high density culture systems incorporating a membrane. Just as screening tools such as 96-well plates and T-flasks have been used to substantially increase the productivity and reliability of stirred-tank bioreactors, a bioreactor of the present invention has the potential to similarly impact hollow fiber bioreactor technology.

Those skilled in the art, given the present description, will be able to identify and use available materials and techniques to fabricate and use bioreactors of this invention.

Oxygen Permeable Tubing.

Oxygen permeable (e.g., silicone rubber) tubing for use in this invention can be obtained or prepared using conventional techniques. The term "oxygen permeable", as used herein, refers to tubing that permits the transfer of oxygen through the tubing, into the medium contained therein in a manner sufficient to support cell growth within the IC space of a hollow fiber bundle. As used herein with respect to the present invention, the word "tubing", and inflections thereof, will refer to a bioreactor shell, of any suitable shape or dimensions, suitable to provide an EC space for medium and an IC space in the form of a hollow fiber bundle.

Such tubing can be formed of any suitable material that provides sufficient oxygen transport, but preferably it is formed of silicone, and more preferably, a silicone rubber. See, for instance, "Silicone Rubbers", Section 29.6, pp. 810–818 in Plastics Materials, $6^{th}$ edition, J. A. Brydson ed. Butterworth Heinemann (1995), the disclosure of which is incorporated herein by reference. Examples of suitable silicone rubbers include modified and unmodified dimethylsilicone rubbers, and liquid silicone rubbers, having an optimal combination of such properties as temperature stability, retention of elasticity, electrical properties, and physiological inertness.

Particularly preferred tubing provides an optimal combination of such properties as oxygen permeability and wall strength. Generally, the oxygen permeability of a silicone tube is inversely proportional to its wall thickness, such that as thickness decreases overall oxygen permeability will increase. Thickness, however, is also directly related to wall strength, such that decreasing thickness will also correspond with the decreased wall strength. Optionally, silicone tubing for use in this invention can be quite thin, provided it is supported or reinforced in a suitable manner. A preferred tubing for use in this invention, therefore, is one that provides an optimal combination of wall strength (supported or unsupported) and oxygen permeability. Overall oxygen flux can be increased, for a given system, by incubating the bioreactor at elevated oxygen concentrations.

Tubing is also preferably able to be sterilized using conventional techniques, such as autoclaving, ethylene oxide, irradiation, and the like. Similarly, tubing for use in fabricating a bioreactor of this invention is preferably biocompatible, e.g., medical grade, in order to facilitate its use in connection with cell growth. Examples of suitable tubing include both peroxide and platinum cured silicones. Preferred tubing is, or can be, certified to meet USP 23 Class VI, or capable of passing an Elution Test such as USP 23, Supplement 5, Monograph 87 (the contents of which are incorporated herein by reference). Preferably, tubing for use in fabricating a bioreactor of this invention provides oxygen permeability of about $100 \times 10^{-10}$ to about $10,000 \times 10^{-10}$ (cc-mm/sec-cm$^2$-cm Hg), and more preferably between about $5,000 \times 10^{-10}$ to about $10,000^{-10}$ (cc-mm/sec-cm$^2$-cm Hg). Suitable materials are preferably flexible, seamless and translucent or transparent, in order to permit the progress to be visualized. Suitable materials are available, for instance, from VWR Scientific (VWR brand SELECT Silicone tubing) and Cole-Parmer (standard silicone tubing). Optionally, tubing for use in fabricating a bioreactor of this invention can be specifically molded to desired dimensions, in which case the molding process can be used to incorporate unique headers and/or fittings for headers.

The optimal dimensions of the tubing, e.g., outer diameter, inner diameter, and in turn, wall thickness can be determined on a case by case basis, for instance, based on the intended use. In the course of fabricating a bioreactor of the present invention, silicone rubber tubing can typically be provided in bulk form, e.g., in rolls. Pieces of suitable size are cut to the desired dimensions, and ports and/or tubes can be placed in desired positions. A suitable tubing can be on the order of about 2 cm to about 30 cm in length. Below about 2 cm the tubing will typically have insufficient capacity for most applications, while above about 30 cm it becomes increasingly difficult to deliver cells suspensions to the hollow fiber bundle, and to fit the entire device in a suitable incubator.

Suitable tubing is also provided with an ID of between about 1/16 inch (about 0.15 cm) and about 1 inch (about 2.5 cm). Tubing having an ID of below about 1/16 inch generally does not provide a sufficient EC reservoir space, while tubing having an ID of greater than about 1 inch generally does not permit suitable transport of oxygen to a hollow fiber bundle centered parallel to and concentric with the central axis of the tubing. Optionally, tubing having an ID of larger than about 1 inch can be used, e.g., where the hollow fiber bundle is splayed along its length in order to bring individual fibers within a suitable distance of the inner wall of the tubing.

Bioreactors are preferably constructed and sealed by a method that provides a durable, waterproof seal yet retains the structural integrity of the bioreactor. Examples of suitable sealing means include the use of an adhesive (e.g., a room temperature vulcanizing ("RTV") silicone glue), interspersed and cured between the opposing membrane surfaces. Examples of suitable adhesives are described, for instance, in Skeist (ed.), *Handbook of Adhesives*, 3rd Ed., Chapt. 30, "Silicone Adhesive Sealants and Adhesives", J. W. Dean, (1990). Alternative sealing means include the use of a clamping mechanism, or integrally forming various components of the bioreactor.

Hollow fibers. Hollow fibers suitable for use in a bioreactor of this invention are commercially available, and can be selected, bundled and positioned using known techniques, given the present description. Suitable hollow fibers provide an optimal combination of such properties as gas permeability, strength, porosity, selectivity and biocompatability.

Suitable hollow fibers include those commonly used for dialysis, ultrafiltration and/or microfiltration applications, e.g., having a molecular weight cut off from about 1 kD to about 1,000 kD, and a pore size from about 0.01 microns to about 5 microns. Suitable hollow fibers can be constructed from a variety of materials, including polymers, graphite, ceramics (including porous glass fiber) and metals (e.g., stainless steel). Preferred are polymeric hollow fibers that provide an optimal combination of such properties as tensile strength, melt temperature, and glass transition temperature. Such hollow fibers can be formed, for instance, from cellulose (including regenerated cellulose and cellulose acetate), polyethylene, polypropylene, polysulfone, polymethyl methacrylate, polyacrylonitrile, poly(vinylidene fluoride) and the like. Suitable regenerated cellulose hollow fibers are available, for instance, under the brand names CUPROPHAN™ (Akzo Nobel, the Netherlands) and HEMOPHAN™ (COBE Laboratories, Inc., Lakewood Colo.) Particularly preferred are fibers having a molecular weight cut off between about 1 kD and about 100 kD, and a pore size of about 0.01 micron and about 1 micron.

Preferred hollow fibers also each provide an inner diameter of between about 20 microns and about 1000 microns, and preferably between about 100 microns and about 500 microns. Above this range, increasing diameters impose diffusional limitations on the cell mass, while below this range, decreasing diameters are more difficult to manufacture and to inoculate with cells. Preferred hollow fibers also each provide a wall thickness of between about 2 microns and about 200 microns, and more preferably between about 5 microns and about 50 microns. Below this range fibers are typically not strong enough to withstand the steps involved in fabricating a bioreactor, while above this range fibers too thick to allow adequate diffusion.

A hollow fiber bundle for use in an apparatus of the present invention will generally include from about 1 to about 1000, and preferably from about 1 to about 100 individual fibers. The fibers can be bundled together in any suitable fashion, e.g., they can be placed adjacent to each other and secured (e.g., glued or sonic welded) together at each end in a manner, and optionally cut through at each end in a manner that permits fluid access into the IC space. The fibers will generally be on the order of the same length as the corresponding silicone tubing, and preferably slightly longer in order to accommodate header space. Preferred hollow fibers are in the form of porous hollow fibers, positioned within the silicone tubing in a manner concentric with the tubing itself. The exterior periphery of the hollow fiber bundle is separated from the inner wall of the silicone housing at a distance sufficient to permit oxygen to pass through the silicone and to the bundle at a rate and amount sufficient to permit cell growth.

Headers. The bioreactor of this invention is preferably provided with substantially identical headers at the input and output ends of the silicone tubing. The headers are used to provide both input and output access to the EC and IC spaces. As such, the EC and IC headers can be provided in the form of separate, dedicated headers, or more preferably, portions of common headers. The EC space headers can be equipped with one or more ports for use in filling the shell with suitable medium, and optionally for withdrawing and replenishing medium, while the IC space headers can be equipped with one or more ports for use in filling the IC space with medium and inoculating cells, and for recovering the resultant cell culture (e.g., by flushing the IC space with compressed gas or liquid).

Headers can be formed of any suitable material, e.g., polypropylene, polycarbonate, and the like, so long as the material is compatible with the tubing and/or hollow fiber material and whatever sealing means may be employed. Particularly preferred are headers that are capable of being sterilized and that provide a low IC dead volume space, since the corresponding cell culture volume is itself typically quite small. Convenient harvesting of cells can be accomplished by introducing a gas or liquid through the first port and flushing the contents from the opposite port. For harvesting anchorage dependent cells, a cell detachment (e.g., proteolytic) enzyme such as trypsin or collagenase can be first introduced into the IC space.

The invention will be further described with reference to the Drawing, wherein FIG. 1 is a comparative schematic showing a simple hollow fiber system (10) of a type known in the art. The medium reservoir (12), bioreactor (14), and gas-exchanger (15) are housed within a $CO_2$ incubator (16). Pumps (18), including peristaltic pump (20) and gassing pump (22) must be placed outside the incubator since the heat from pump operation tends to raise the incubator temperature. Bioreactor (14) contains a multitude of hollow fibers, with cells being cultured outside of those fibers and within the extracapillary (EC) space. Medium is circulated with a peristaltic pump from the reservoir, through the gas-exchanger (14), through the inside of the bioreactor fibers in the intracapillary (IC) space, and is returned back to the reservoir. The gassing pump continually draws the humidified air/$CO_2$ atmosphere of the incubator through the gas-exchange cartridge to oxygenate the medium and buffer the medium pH.

Figure 2:
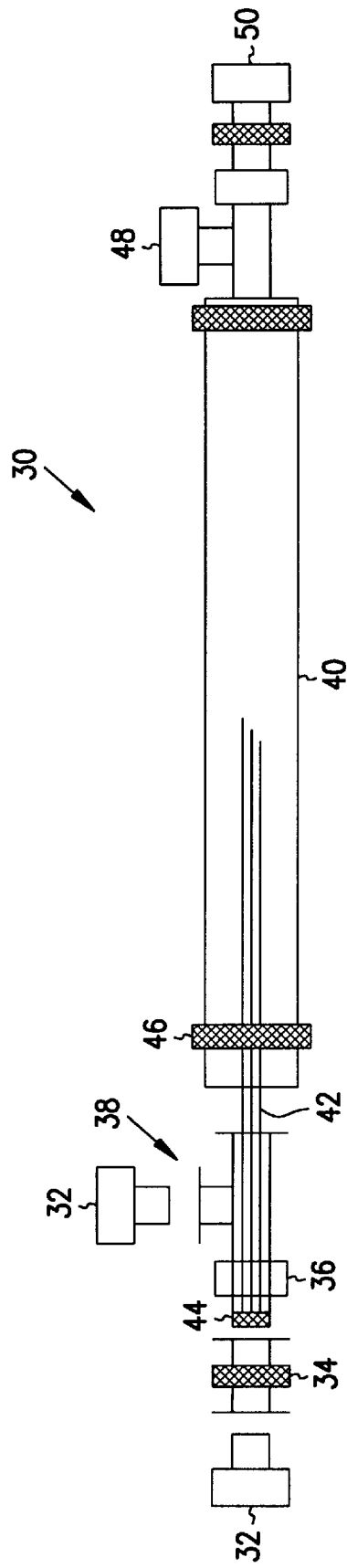
FIG. 2 depicts a schematic of a 4 ml hollow fiber bioreactor, wherein the left side shows an exploded view and the right side shows an assembled view.

Turning to FIG. 2, there is shown a schematic of a small (e.g., 4 ml EC capacity) bioreactor (30) of the present invention. The left side of FIG. 2 represents an exploded view, while the right side shows an assembled view. Included in the bioreactor are a male plug luer with cap (32), a female/female luer (34), a rotating lock ring (36), a female/female/male T luer (38), a piece of silicone tubing (40), a hollow fiber bundle (42), silicone potting sealant (44) and a tie strap (46). Shown in assembled form on the left, these components provide a EC access port (48) and an IC access port (50). In order to prepare a larger bioreactor (e.g., up to 100 ml EC capacity), the inner diameter (ID) of the silicone tubing is preferably selected or adjusted in order to provide a snug and sealed fit between the ends of the fiber bundle, the end caps and the silicone tubing. For instance, a larger piece of silicone tubing can be placed circumferentially over a smaller piece and snugly fit in order to seal the two.

Figure 3A:
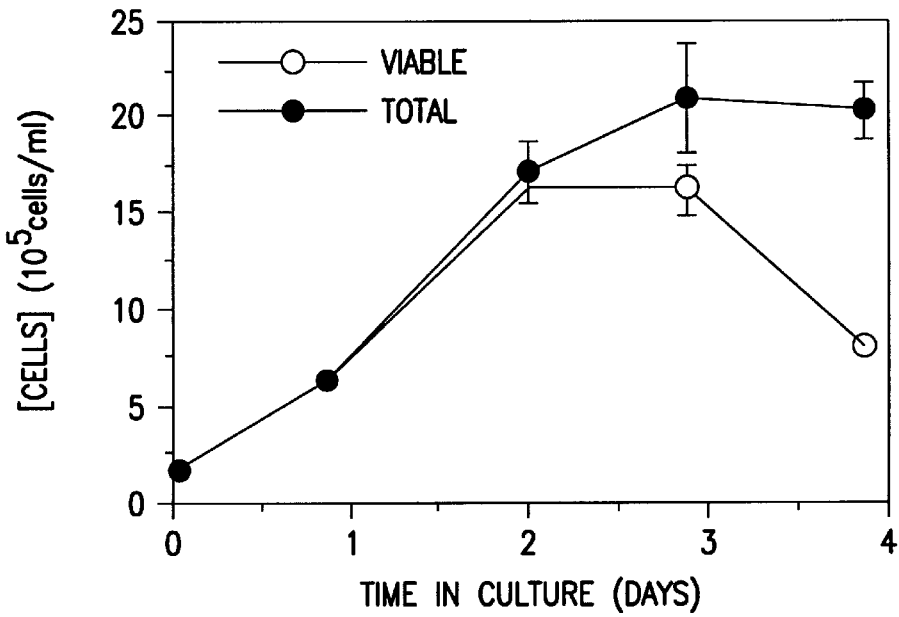
FIGS. 3 and 4 show growth curves for rho 1D4 hybridoma cells in both T-flasks (FIG. 3) and in a bioreactor of this invention (FIG. 4).
Figure 3B:
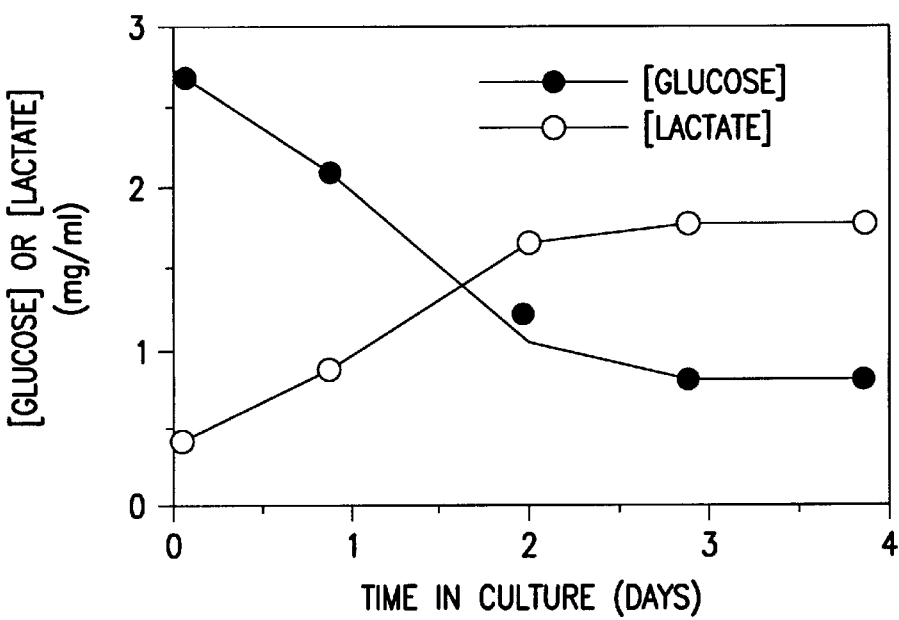
Figure 3C:
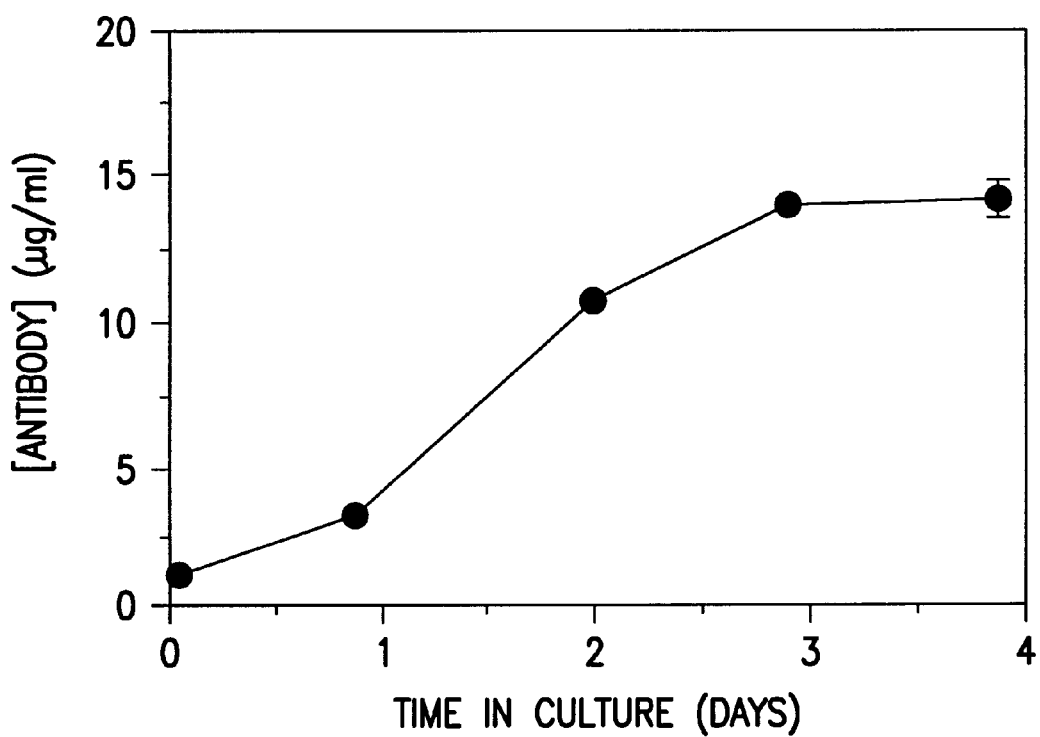
Figure 4A:
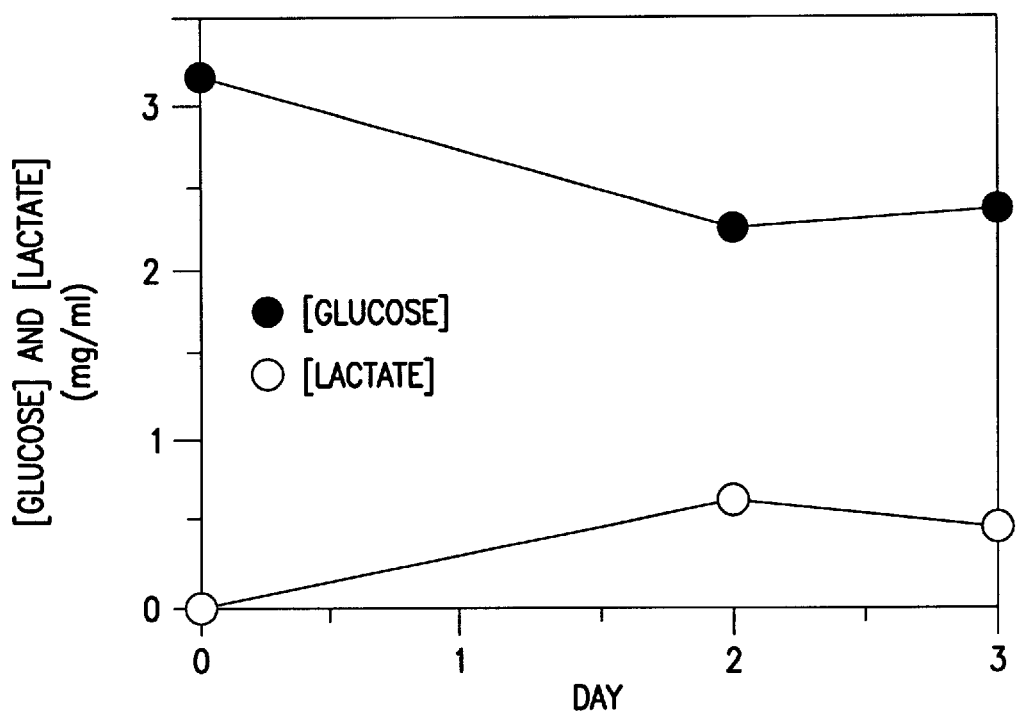
Figure 4B:
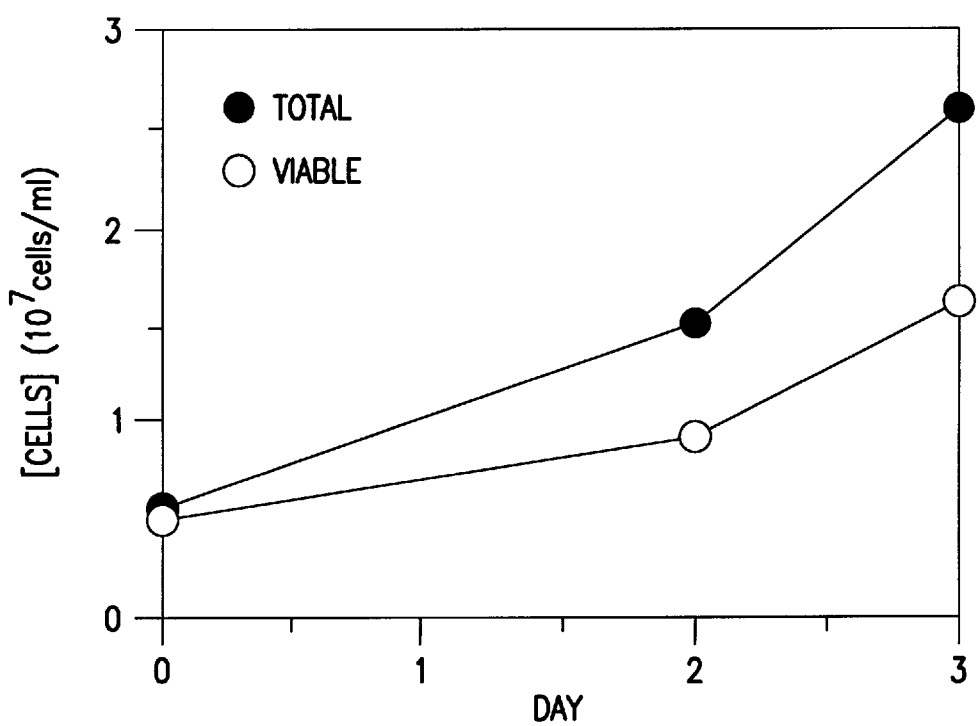
Figure 4C:
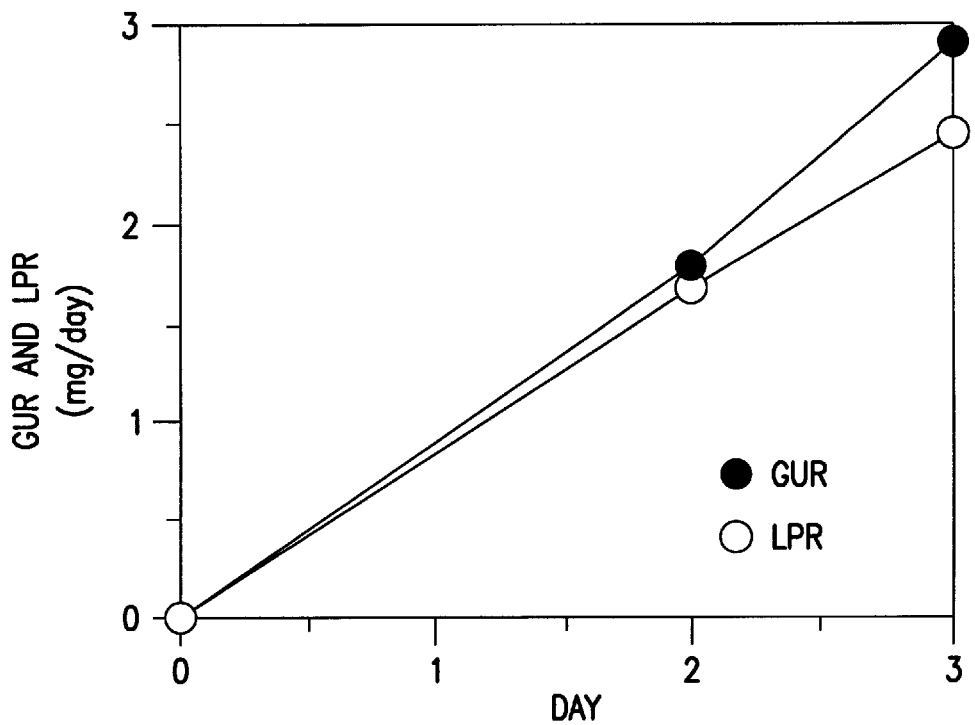
Figure 4D:
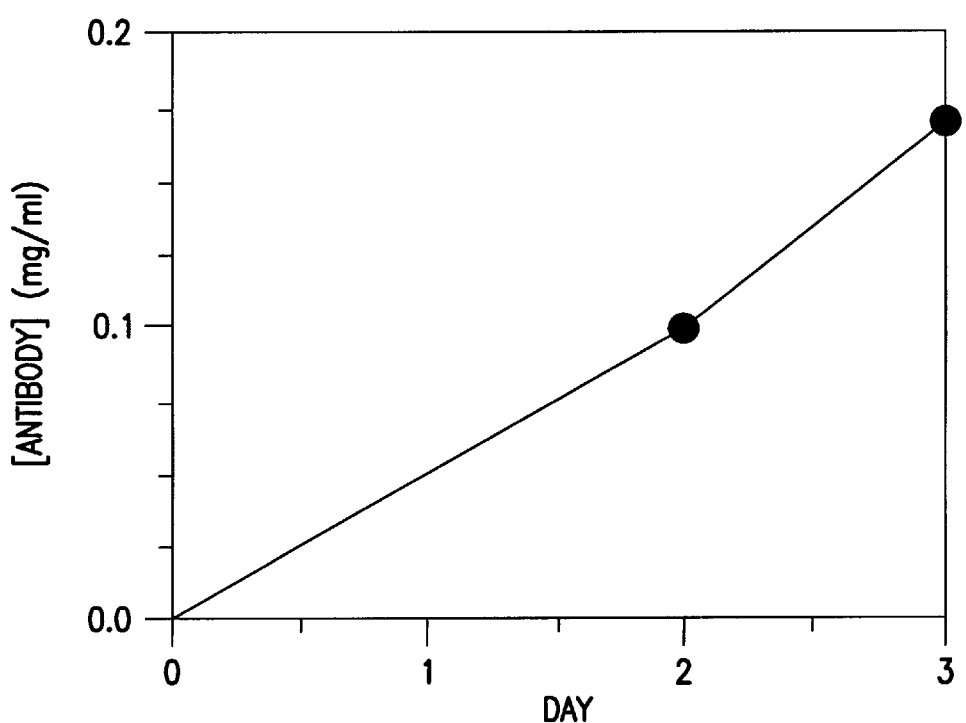
Figure 5A:
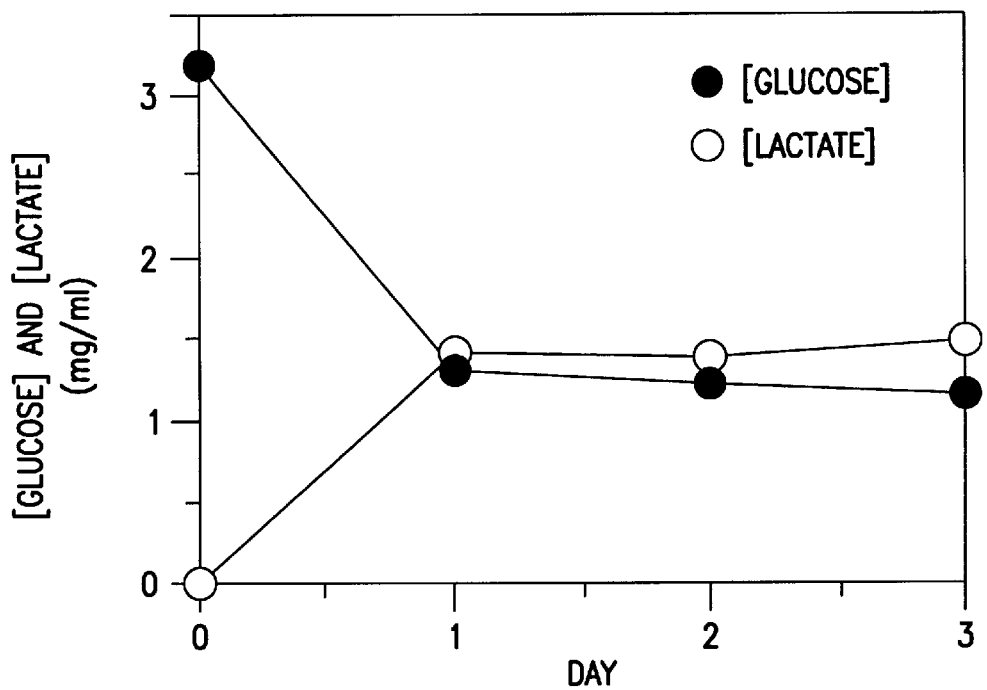
FIG. 5 shows a growth curve for hybridoma cells inoculated in a bioreactor at high density.
Figure 5B:
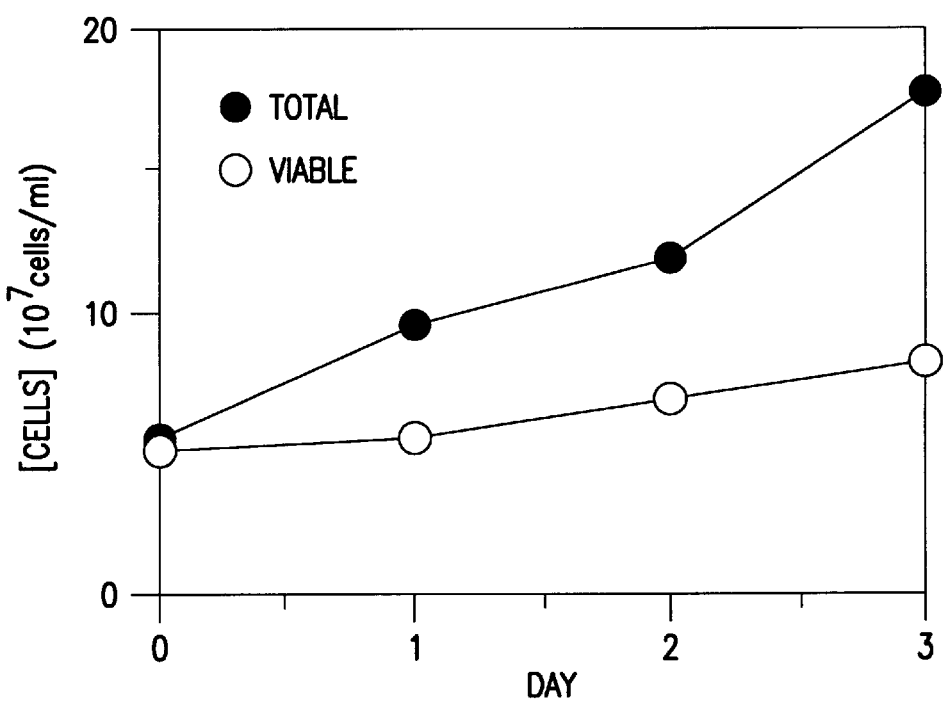
Figure 5C:
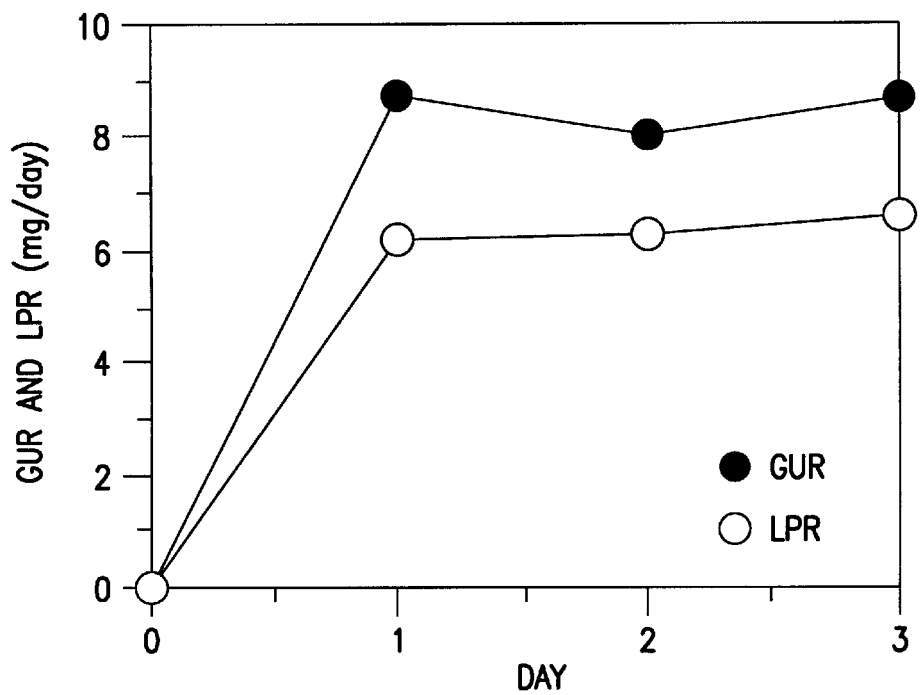
Figure 5D:
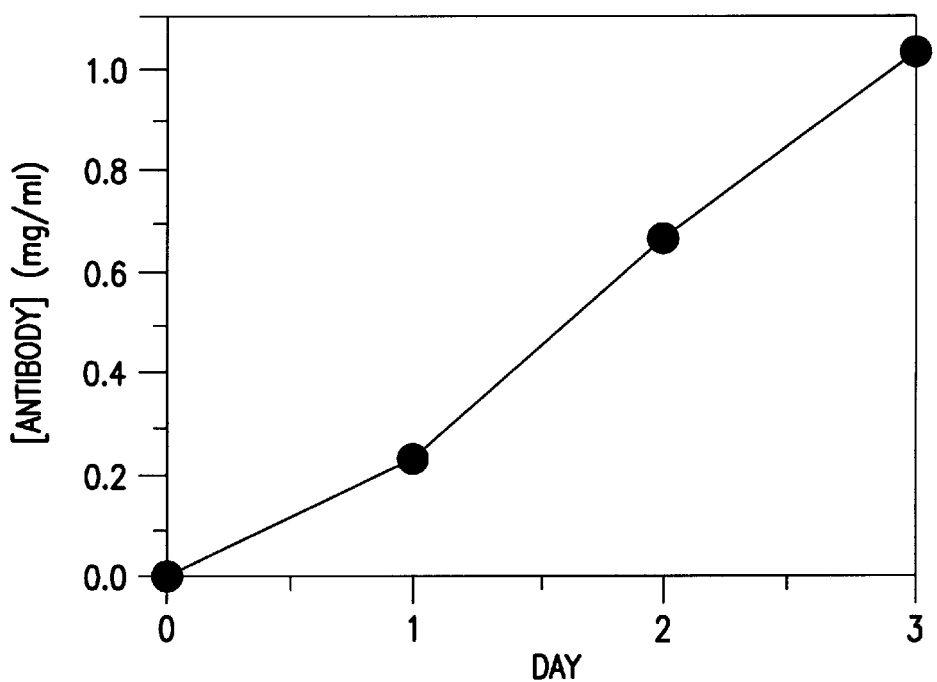

FIGS. 3 and 4 show growth curves for rho 1D4 hybridoma cells in both T-flasks and a bioreactor, respectively. In the experiment leading to FIG. 3, cells were inoculated at $2\times10^5$/ml in triplicate T75 flasks with 20 ml of 10% serum-supplemented medium. Samples were taken daily for analyses, and the average and standard deviation of the results are shown. In FIG. 4, by contrast, cells were inoculated in the IC (0.2 ml culture space) of three bioreactors of the present invention at $5\times10^6$/nml with 10% serum-supplemented medium. The EC contained 4 ml basal medium. On day 2, the EC medium was changed, and the IC medium was harvested from one bioreactor for cell counts and antibody assay. On day three, the EC and IC media from the remaining two bioreactors were harvested. Data shown are averaged results (GUR, glucose uptake rate; LPR lactate production rate).

Turning next to FIG. 5, there is seen a growth curve for hybridoma cells inoculated at high density. Cells were inoculated in the IC (0.2 ml culture space) of three bioreactors of this invention, at $5\times10^7$/ml with 10% serum-supplemented medium. The EC contained 4 ml basal medium. The IC medium from one bioreactor was harvested daily for cell counts and antibody assay. EC medium was changed daily on the remaining bioreactors. Data shown are averaged results (GUR, glucose uptake rate; LPR lactate production rate).

Figure 6:
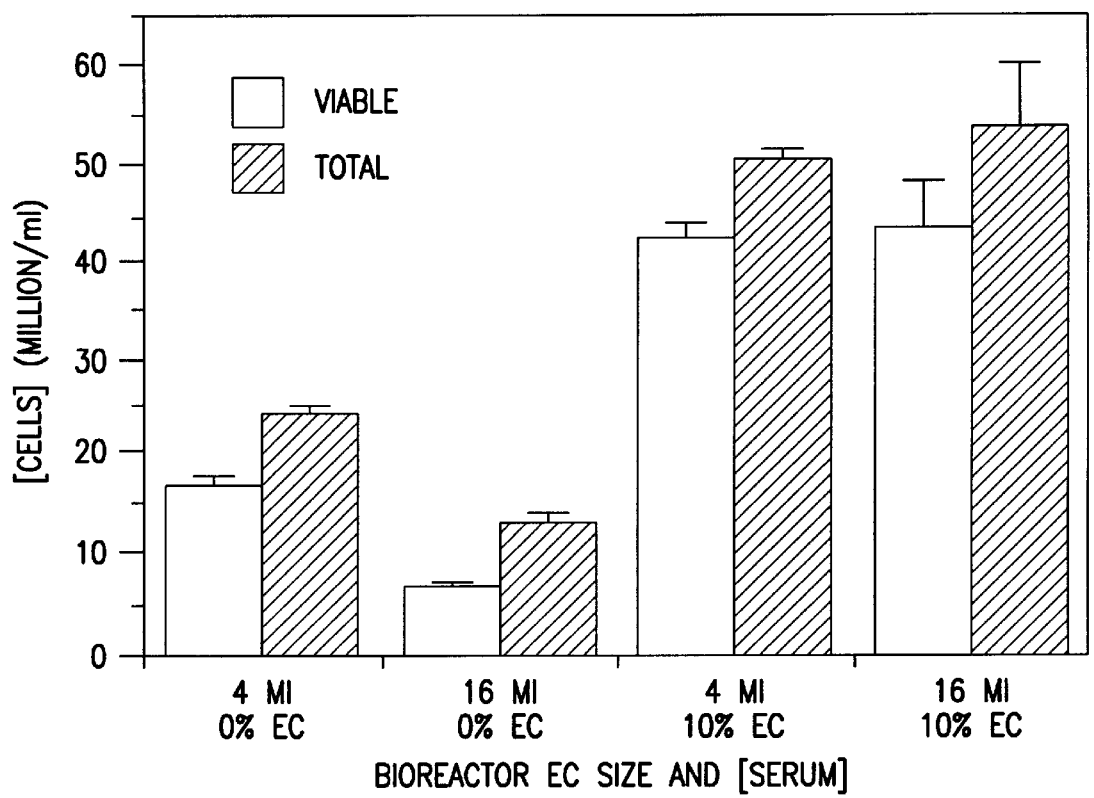
FIG. 6 shows a bar graph to demonstrate the effect of bioreactor EC size and medium on cell growth in the bioreactor.

FIG. 6, in turn, shows the effect of bioreactor EC size and medium on cell growth in a bioreactor of the present invention. Cells were inoculated in 10% serum-supplemented medium at $5\times10^6$/ml in the bioreactor IC (0.2 ml culture space), and harvested three days later. The EC space was 4 or 16 ml, and contained basal medium (0% EC) or 10% serum-supplemented medium (10% EC). Data shown are the averages and standard deviations of duplicate bioreactors.

Figure 7:
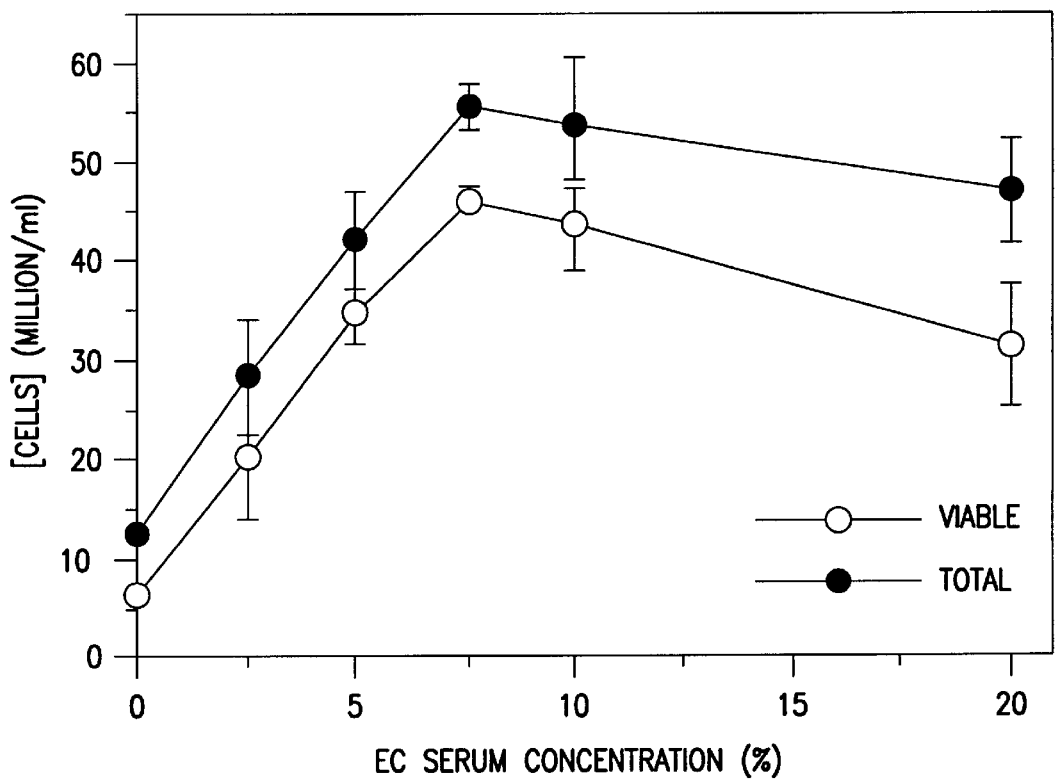
FIG. 7 shows a curve to demonstrate the effect of EC serum concentration on cell growth in 16-ml bioreactors.

Similarly, FIG. 7 shows the effect of EC serum concentration on cell growth in 16-ml bioreactors. Cells were inoculated at $5\times10^6$/ml in 10% serum-supplemented medium in the IC with varying concentrations of serum in the EC medium. Bioreactors were harvested three days later. Data shown are the averages and standard deviations of duplicate bioreactors.

Figure 8:
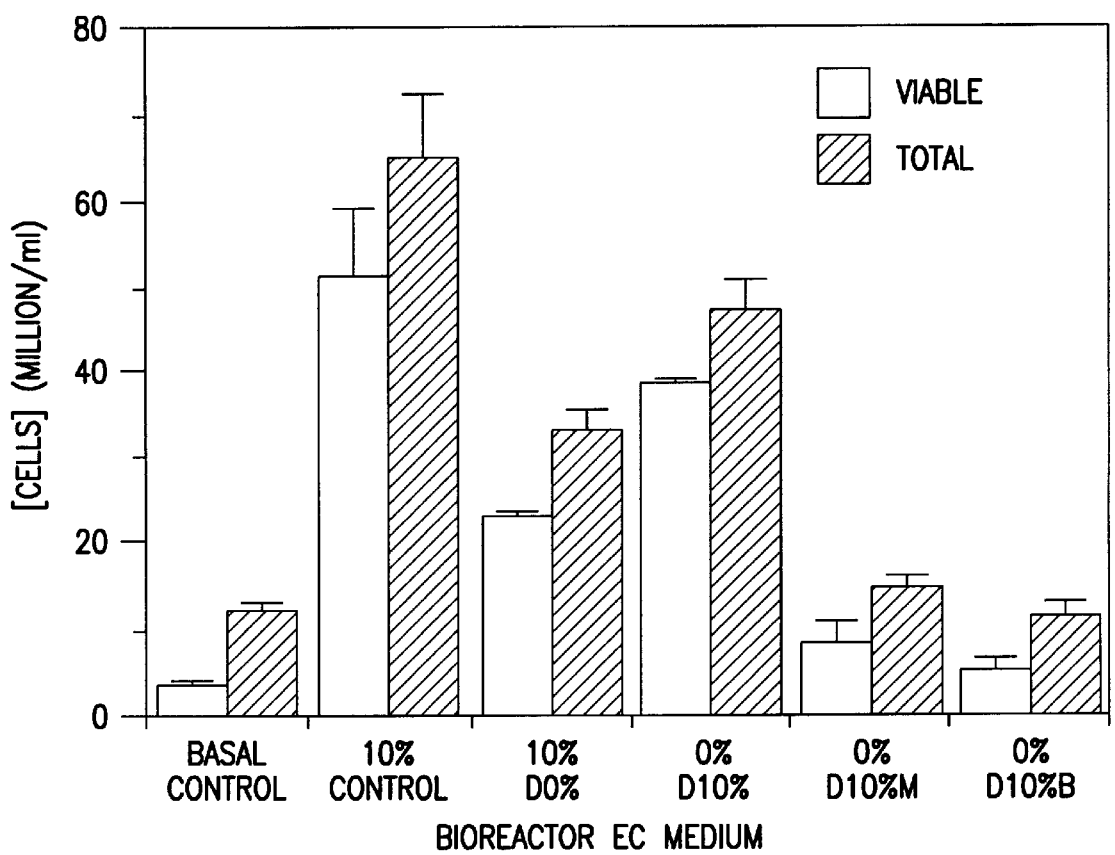
FIG. 8 shows a bar graph to demonstrate the effect of EC medium dialysis on cell growth in 16-ml bioreactors.

The results in FIG. 8 show the effect of EC medium dialysis on cell growth in 16 ml (EC space) bioreactors of this invention. The bioreactor EC was filled with medium and dialyzed by circulating 1280 ml per bioreactor through the IC for one week. EC medium containing 10% serum was dialyzed against basal medium (10% D0%), while basal EC medium was dialyzed against 10% serum (0% D10%). The basal media from some of the bioreactors dialyzed against 10% serum were transferred to new bioreactors (0% D10% M), and the empty bioreactors were filled with fresh basal medium (0% D10% B). The control bioreactors were not dialyzed. Cells were inoculated at $5\times10^6$/ml in 10% serum-supplemented medium in the IC, and were harvested three days later. Data shown are the averages and standard deviations of duplicate bioreactors.

Figure 9A:
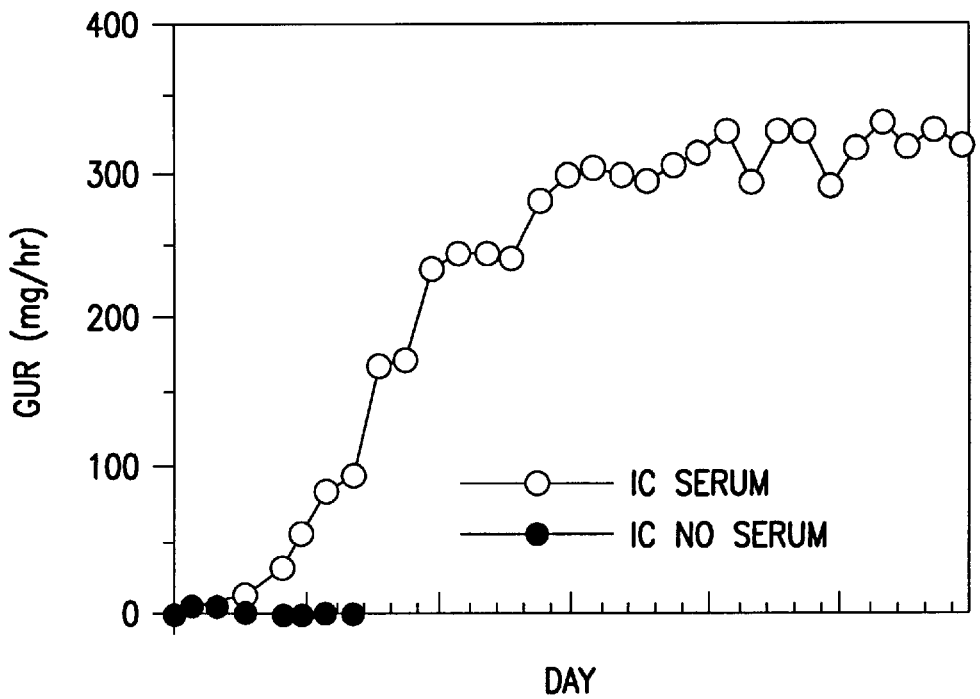
FIG. 9 shows curves of glucose utilization rate and antibody concentration over time.
Figure 9B:
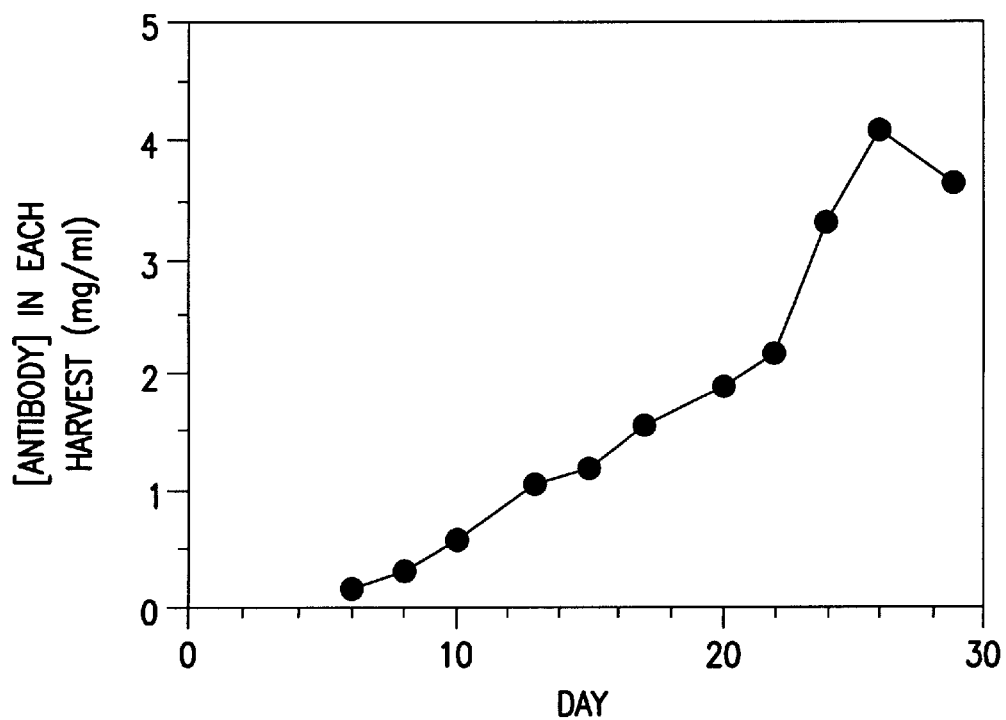

Finally, FIG. 9 shows the effect of IC serum addition on the growth of rho 1D4hybridoma cells in the ResCu Primer-HF. Cells were inoculated in the EC space of two bioreactors at $5\times10^6$/ml with 10% serum. The IC medium reservoir of one bioreactor contained 10% serum, while the IC reservoir of the other bioreactor contained only basal medium. The top graph shows the glucose utilization rate (GUR) for each bioreactor. The bioreactor without serum in the IC was discontinued after day 7 due to poor cell growth. Serum was gradually removed from the other system between days 7 and 11 (a reduction of 2% serum per day), and the cells continued to grow. The antibody concentration of each 20-ml EC harvest is shown in the bottom graph only for the bioreactor which initially contained serum in the IC.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by volume.

EXAMPLES

Cells and Media. The rho 1D4 murine hybridoma cell line (obtained from the National Cell Culture Center, Minneapolis, Minn.) secreting anti-rhodopsin IgG antibody was used for this study (Molday and MacKenzie, "Monoclonal Antibodies to Rhodopsin: Characterization, Cross-Reactivity, and Application as Structural Probes", *Biochemistry* 1983, 22, 653–660). This hybridoma was formed from the fusion of spleen cells from an immunized Balb/c mouse with the NS-1 myeloma fusion partner. Basal medium (Sigma Chemical Company) consisted of Dulbecco's Modified Eagle's Medium and Ham's Nutrient mixture F12 ("DME/F12") with 2.5 mM L-glutamine, 2.44 g/L sodium bicarbonate, 0.066 g/L penicillin G (Irvine Scientific), and 0.144 g/L streptomycin sulfate (Irvine Scientific). Serum-supplemented medium was prepared by adding fetal bovine serum (Sigma) to basal medium. Cells were routinely propagated in 10% serum-supplemented medium at 37° C. in a humidified incubator with 5% $CO_2$. Cells were passaged every 1 to 3 days.

Assays. The viable and total cell concentrations were determined with a hemacytometer using trypan blue. Glucose and lactate concentrations were measured with a YSI 2700 Select Bioanalyzer (Yellow Springs Instruments). Antibody concentrations were determined by sandwich ELISA with a polyclonal goat anti-mouse IgG antibody and polyclonal goat antimouse IgG antibody labeled with peroxidase (Sigma); color was developed with 2,2'-azinobis(3-ethylbenzthiazoline-sulfonic acid) ("ABTS"). Dissolved oxygen concentration and pH were measured using an AVL 990 blood-gas analyzer (AVL Scientific).

Characterization of Growth in a T-flask. The rho 1D4 cell line in exponential growth was inoculated at $2 \times 10^5$ cells/ml in triplicate T-75 flasks (Coming) with 20 ml medium. One ml of medium was withdrawn from each flask daily for analyses. Cells in the sample were counted, the sample was centrifuged at 7000×g for 5 min., and the supernatant was frozen for later analysis of glucose, lactate, and antibody concentrations.

Bioreactor. The bioreactors were constructed by passing 30 fibers through a 15-cm piece of silicone tubing, and by potting each fiber end in a polycarbonate T luer fitting with silicone adhesive (GE RTV118) as shown in FIG. 2 (all luer fittings were from Value Plastics). The fibers were cut flush with the T fitting with a razor blade 24 hours after applying the adhesive. The bioreactor was pressure tested for leaks by applying 200 mm Hg air pressure to the IC compartment with no caps on the EC ports. The bioreactors were sterilized by ethylene oxide gas without caps in sterility bags. The caps were autoclaved separately and added to the bioreactors aseptically in a hood.

The fibers were made of regenerated cellulose (Cuprophan™) with a 10 kD molecular weight cut off, a 0.02 cm ID, and a 0.022 cm OD. After trimming, the total fiber length was about 20 cm (with about 2.5 cm of fiber on each end encapsulated in adhesive). The total surface area of the fibers (not in adhesive) based on fiber ID was about 29 $cm^2$ with a total IC volume of about 0.2 ml. The EC volume depended on the diameter of the silicone tubing. Two sizes were used in this study including a 4-ml bioreactor (silicone ID 0.635 cm, OD 1.11 cm) and a 16-ml bioreactor (silicone ID 1.27 cm, OD 1.191 cm). The bioreactors were flushed before use to remove the wetting agent in the fibers and residuals from the sterilization process.

First, the IC was flushed and filled by passing 2 ml of basal medium through one end with a syringe while collecting the excess on the other end with another syringe. The EC was then filled with medium using a syringe, and the bioreactor was allowed to sit for 2 to 24 hours. Just before use, the EC medium was removed and the IC was primed with 10% serum-supplemented medium by passing 1 to 2 ml through with syringes. The bioreactor EC was then rinsed with one volume of culture medium, filled with culture medium, and placed in an incubator for 2 hours to warm up and equilibrate with the $CO_2$. Cells were passaged daily for three days leading up to each experiment to maintain an exponential growth phase with viability above 95%.

For inoculation, cells at about $5 \times 10^5$/ml were pelleted by centrifugation at 200×g, and were resuspended in fresh 10% serum supplemented medium at $5 \times 10^6$ or $5 \times 10^7$/ml. The cell suspension was taken up in a syringe using a 16-gauge needle, 0.5-ml of the suspension was passed through the IC of each bioreactor (pushing in with one syringe while pulling out with another on the other end), and the bioreactors were placed in an incubator. Cells were harvested 1 to 3 days later by injecting air in one IC port with a 1-ml syringe while collecting the effluent from the opposite port with another 1-ml syringe. A sample of the IC harvest was used for cell counts; the remainder was centrifuged at 7,000×g and the supernatant was frozen for later ELISA analysis. An EC medium sample was also taken for analysis of glucose, lactate, pH and dissolved oxygen.

Production Hollow fiber Bioreactor. The production hollow fiber bioreactor used was a ReCu-Primer HF (CELLEX BIOSCIENCES). The flow path for this bioreactor is shown in FIG. 1. The bioreactor fibers were Hemophan™ which is similar to Cuprophan™, except that a portion of the glucose polymer free hydroxyls are substituted with a DEAE group which adds a positive charge to the fiber. The fibers had a 10 kD molecular weight cut off, and the total surface area based on fiber ID) was 2200 $cm^2$. The EC volume of the bioreactor was 85 ml. The gas-exchange cartridge was manufactured from 0.12 $M^2$ of silicone membrane. The bioreactor was flushed with basal medium by pumping 2 L simultaneously through the IC and EC compartments over a 4-hour period with no recirculation.

The IC was primed w with culture medium (either basal medium or basal medium plus 10% fetal bovine serum), and a 200-ml reservoir of culture medium was placed on the IC side. The EC side was primed with 10% serum-supplemented medium by injecting 60 ml into the top port while removing 60 ml from the bottom port. For inoculation, a total of $2 \times 10^8$ cells in exponential growth at about $5 \times 10^5$ cells/ml were pelleted at 200×g and resuspended in 15 ml of fresh 10% serum-supplemented medium. The 15-ml cell suspension was added to the top EC port of the bioreactor with a syringe while removing an equal volume of medium through the bottom EC port with a second syringe. The medium collected in the bottom syringe was then slowly inserted transmembrane in to the bioreactor (ultrafiltered to the IC side) after closing the top clamp. An additional 5-ml fresh 10% serum-supplemented medium was then added to the bioreactor transmembrane through the top EC port to flush the inoculum from the top port.

The IC medium recirculation rate was initially 80 ml/min, and was increased up to 200 ml/min to keep the dissolved oxygen concentration at the bioreactor outlet above 60 mm Hg. Media bottles were changed as needed to keep the glucose concentration above 1.5 g/L, or automatically after two days regardless of glucose concentration. The volume of medium in the bottle was increased up to 2 L to support the glucose demand, after which the medium was supplemented with an additional 2 mM L-glutamine, 1 g/L glucose and 1 g/L sodium bicarbonate. The EC medium was changed 3 times per week by adding 20 ml of 10% serum-supplemented medium through the bottom port while harvesting 20 ml through the top port. Cells in the EC harvest were counted, and the supernatant from a sample centrifuged at 7000×g was frozen for later ELISA analysis.

T-flask Growth Curve. Growth of the rho 1D4 hybridoma cell line was first characterized in T-flasks. The cells reached a maximum density of $2\times10^6$ cells/ml with an antibody concentration of 15 μg/ml (FIG. 3).

Bioreactor Operation. Cells are inoculated inside the fibers (IC space) of a (0.2 ml) hollow fiber bioreactor of this invention, having a volume of 0.2 ml, and the bioreactors are placed in a 37° C. incubator with 5% $CO_2$. The space between the fiber and the silicone tubing (EC space) is used as a medium reservoir (4 or 16 ml depending on tubing size) to supply nutrients for at least a 24-hour period. Gas exchange ($O_2$ $CO_2$) occurs directly through the silicone tubing. The fibers allow passage of nutrients below about 10 kD. Typically, basal medium with serum (or high molecular weight growth factors) is supplied on the cell side of the membrane while only basal medium is supplied on the other side of the membrane. Because of the cell culture volume, only a small number of cells are necessary to inoculate at low density ($5\times10^6$/ml) to simulate the growth phase or at high density ($5\times10^7$/ml to $5\times10^8$/ml) to simulate the stationary phase of production scale hollow fiber systems. As a result, the performance of the cell line in both the growth and stationary phases can potentially be assessed in a few days.

Characterization of Cell Growth. The rho 1D4 hybridoma cell line was inoculated in 10% serum-supplemented medium into the IC space of three bioreactors at the typical inoculation density of $5\times10^6$/ml (FIG. 4). On day 2, the 4 ml of basal EC medium was changed on all three bioreactors, and the IC medium on one bioreactor was harvested for analysis of cell growth and antibody concentration. The other two bioreactors were harvested on day 3. As shown in FIG. 4, the bioreactor supported good growth over the 3-day period with increasing cell density, metabolic activity, and antibody concentration. Cells were similarly inoculated into three bioreactors at $5\times10^7$/ml (FIG. 5). The 4 ml of basal EC medium was changed daily, and one bioreactor was harvested each day for cell counts and antibody assay. The cell density increased to almost $2\times10^8$/ml and the antibody concentration to over 1 mg/ml over the 3-day period (FIG. 5). This is typical of confluent production scale hollow fiber systems (Piret and Cooney, "Mammalian Cell and Protein Distributions in Ultrafiltration Hollow Fiber Bioreactors". *Biotech. Bioeng.* 1990, 36, 902–910). The pH and dissolved oxygen concentrations were in acceptable ranges for all the bioreactors in FIG. 4 and FIG. 5 (pH 6.9–7.2, $pO_2$ 120–140 mm Hg).

Effect of EC Medium Volume and Serum Concentration. The glucose uptake rate and lactate production rate did not increase over the 3-day period of high density inoculation, and the cell viability was only 50% (FIG. 5). To determine if this could be due to a limiting basal medium component, the EC volume was increased to 16 ml by using a piece of silicone tubing with twice the diameter. Cells were inoculated in the IC in 10% serum-supplemented medium at $5\times10^6$/ml in 16 ml bioreactors using 4-ml bioreactors as controls, and the bioreactors were harvested after three days. Somewhat surprisingly, cell growth in the 16-ml bioreactors was very poor (FIG. 6). This poor growth was not due to oxygen limitations since recirculation of the EC medium did not result in better cell growth or viability (not shown). These results could potentially be explained by a dilution effect if important serum components are crossing the membrane from the IC to the EC space. To test this possibility, 10% serum-supplemented medium was added to the EC side as well as the IC side of the 4- and 16-ml bioreactors. Cell growth and viability in both bioreactors containing serum on the EC side were essentially identical (FIG. 6), and substantially better than both bioreactors which did not contain serum on the EC side. Glucose consumption, lactate production, and antibody productivity followed similar trends (not shown).

To explore the effect of EC serum concentration, cells were inoculated in a series of 16-ml bioreactors at $5\times10^6$/ml with EC serum ranging from 0 to 20% (the IC side with the cells always contained 10% serum). All bioreactors were harvested after 3 days. Cell growth increased with increasing serum concentration up to about 7.5 to 10% serum, and decreased slightly at 20% serum (FIG. 7). Glucose consumption, lactate production, and antibody productivity followed similar trends (not shown).

Effect of Dialysis. The above data support the hypothesis that one or more serum components important for cell growth can dialyze across the fiber membrane. When basal medium is placed in the EC, these components are diluted from the IC, effectively reducing the concentration of these components to suboptimal levels within the cell culture space. Placing serum in the EC eliminates this dilution effect.

To test this hypothesis more directly, bioreactors were flushed, and the EC space ws filled with 16 ml of 10% serum-supplemented medium. The EC media in these bioreactors were dialyzed against 1280 ml of basal medium each by recirculating the medium from a bottle through the IC of each bioreactor at a rate of 2 ml/min for one week at 4° C. (the 16:1280 ml ratio is the same as the IC/EC ratio of 0.2/16). After this time, the glucose and lactate concentrations in the IC and EC had equilibrated (data not shown). Control bioreactors with the EC containing basal medium or 10% serum-supplemented medium were kept at 4° C. for one week, but were not dialyzed. Cells were inoculated at $5\times10^6$/ml in the IC of each bioreactor in 10% serum-supplemented medium, and the bioreactors were harvested three days later for cell counts.

The bioreactor with dialyzed serum-supplemented medium (10% D0%) did not support cell growth as well as the 10% EC serum control (10% Control), demonstrating that some of the important growth factors can be dialyzed away (FIG. 8). However, cell growth in the 10% D0% bioreactor was better than cell growth in the basal EC control (0% Control), suggesting that simple dialysis cannot efficiently remove all the factors in serum important for cell growth (FIG. 8). These results could potentially be explained by the presence of important soluble components that are easily dialyzed and the presence of important hydrophobic components that could be retained by hydrophobic carriers (or by a partially soluble component). For example, fatty acids are only sparingly soluble and are tightly bound by albumin (Spector, "The Transport and Utilization of Free Fatty Acids". *Ann. N.Y. Acad. Sci.* 1968, 149, 768–783). As a result, dialysis of the fatty acids would be inefficient.

To be consistent with this hypothesis, the poor growth in bioreactors containing basal EC medium has to be explained by simple dialysis and the presence of a hydrophobic carrier. However, basal medium does not contain a hydrophobic carrier. Therefore, the possibility that the silicone tubing in the bioreactor was acting as a hydrophobic reservoir was tested. In an experiment similar to the one above, bioreactors with 16 ml of basal EC medium were each dialyzed against 1280 ml of 10% serum-supplemented medium. To determine whether the silicone tubing is important for the partitioning of medium components, the media from some of these dialyzed bioreactors were transferred to new bioreactors, and fresh basal medium was added to the empty dialyzed bioreactors. Therefore, hydrophobic components will potentially remain adsorbed to the silicone tubing in the original bioreactor, while soluble components will be transferred to the new bioreactor in the dialyzed medium. The bioreactors in this experiment were dialyzed and inoculated simultaneously with those in the previous experiment, and share the controls shown in FIG. 8. The bioreactors with basal EC medium dialyzed against 10% serum (0% D10%) supported substantially better cell growth compared to the basal medium control (0% Control) (FIG. 8). However, when the dialyzed medium (0% D10% M) and bioreactor (0% D10% B) are split up, neither bioreactor supports good cell growth (FIG. 8). These results suggest that poor cell growth in the bioreactors with basal EC medium is due to the dilution of IC serum components across the 10 kD fiber membrane; a fraction of these components remain soluble in the EC medium, while another fraction is adsorbed to the silicone tubing, and the two fractions have a synergistic effect on cell growth. This is important because the gas exchange cartridges of larger systems are often made of hydrophobic materials such as silicone or polypropylene.

Hollow fiber Production System. The bioreactor results suggest that the rho 1D4 hybridoma cell line will perform better if 10% serum is used on both sides of the membrane. To test this prediction, two production hollow fiber systems (FIG. 1) were inoculated simultaneously; one used 10% serum on the cell side only (EC), while the other used 10% serum in both the EC and IC compartments. The glucose uptake rates in the two bioreactors were similar for the first 24 hours (FIG. 9). However, cells in the bioreactor without serum on both sides of the membrane died shortly thereafter, and this bioreactor was discontinued after 7 days. Alternatively, the bioreactor with 10% serum on both sides of the membrane supported good cell growth. Serum was gradually weaned from the system IC between 7 and 11 (a reduction of 2% serum per day), but the metabolic activity of the cells continued to increase. This entire experiment was repeated with similar results (not shown). This data confirms that components in serum that can cross the membrane are essential for the initial growth phase of this cell line in a production system. This data also demonstrates that the bioreactor can be used to predict the performance of a cell line in a scaled up hollow fiber bioreactor system.

What is claimed is:

1. A hollow fiber bioreactor comprising:
   a) oxygen permeable tubing having first and second ends, wherein the tubing provides oxygen permeability of between about $100 \times 10^{-10}$ to about $10,000 \times 10^{-10}$ (cc-mm/sec-cm$^2$ -cm Hg);
   b) one or more hollow fibers disposed within and traversing the length of the tubing in order to provide an intracapillary space and an extracapillary space, and
   c) first and second headers disposed at the first and second ends of the tubing, respectively, for scalably securing the one or more hollow fibers and for permitting the passage of substances into the intracapillary space and/or extracapillary space wherein, the extracapillary space provides a medium reservoir of about 1 ml to about 100 ml and the intracapillary space provides a cell culture volume of about 0.1 ml to about 1 ml;
   wherein the bioreactor lacks a pump for the delivery of oxygen or medium to the intracapillary or extracapillary spaces.

2. A bioreactor according to claim 1 wherein the tubing is formed of silicone rubber tubing.

3. A bioreactor according to claim 1 wherein the hollow fibers provide a molecular weight cut off from about 1 kD to about 1,000 kD.

4. A bioreactor according to claim 1 wherein the hollow fibers provide a pore size from about 0.01 microns to about 5 microns.

5. A bioreactor according to claim 1 wherein the hollow fibers are formed of a material selected from the group consisting of cellulose, polyethylene, polypropylene, polysulfone, polymethyl methacrylate, polyacrylonitrile, and poly(vinylidene fluoride).

6. A bioreactor according to claim 1 wherein about 1 to about 1000 individual fibers are provided.

7. A bioreactor according to claim 1 wherein the tubing provides oxygen permeability of between about $5,000 \times 10^{-10}$ to about $10,000^{-10}$ (cc-mm/sec-cm$^2$ -cm Hg).

8. A bioreactor according to claim 7 wherein the tubing is flexible, seamless and translucent or transparent.

9. A method of evaluating cell growth in vitro, the method comprising the steps of
   a) providing a bioreactor according to claim 1,
   b) inoculating the intracapillary space with the cells and a suitable medium and filling the extracapillary space with a suitable medium,
   c) incubating the bioreactor under conditions suitable to permit oxygen transfer through the tubing and to the hollow fiber bundle, and
   d) evaluating cell growth in the intracapillary space.

10. A method according to claim 9 wherein the bioreactor tubing is formed of silicone rubber tubing.

11. A method according to claim 9 wherein the bioreactor hollow fibers provide a molecular weight cut off from about 1 kD to about 1,000 kD.

12. A method according to claim 9 wherein the hollow fibers provide a pore size from about 0.01 microns to about 5 microns.

13. A method according to claim 9 wherein the hollow fibers are formed of a material selected from the group consisting of cellulose, polyethylene, polypropylene, polysulfone, polymethyl methacrylate, polyacrylonitrile, and poly(vinylidene fluoride).

14. A method according to claim 9 wherein the hollow fibers are provided in a bundle comprising from about 1 to about 1000 individual fibers.

15. A method according to claim 9 wherein the tubing provides oxygen permeability of between about $5,000 \times 10^{-10}$ to about $10,000 \times 10^{-10}$ (cc-mm/sec-cm$^2$ -cm Hg).

16. A method according to claim 15 wherein the tubing is flexible, seamless and translucent or transparent.

* * * * *